(12) United States Patent
Carter et al.

(10) Patent No.: US 11,204,307 B2
(45) Date of Patent: Dec. 21, 2021

(54) IN-SITU SOLID ROCKET MOTOR PROPELLANT GRAIN AGING USING GAS

(71) Applicant: GOODRICH CORPORATION, Charlotte, NC (US)

(72) Inventors: Joshua David Carter, Fairfield, CA (US); Kevin Mueller, Dixon, CA (US)

(73) Assignee: Goodrich Corporation, Charlotte, NC (US)

( * ) Notice: Subject to any disclaimer, the term of this patent is extended or adjusted under 35 U.S.C. 154(b) by 247 days.

(21) Appl. No.: 16/386,186

(22) Filed: Apr. 16, 2019

(65) Prior Publication Data
US 2020/0333224 A1    Oct. 22, 2020

(51) Int. Cl.
*G01N 3/10* (2006.01)
*F02K 9/38* (2006.01)

(52) U.S. Cl.
CPC .......... *G01N 3/10* (2013.01); *F02K 9/38* (2013.01); *F05D 2220/80* (2013.01); *F05D 2260/83* (2013.01); *G01N 2203/0044* (2013.01); *G01N 2203/0212* (2013.01); *G01N 2203/0274* (2013.01); *G01N 2203/0676* (2013.01)

(58) Field of Classification Search
CPC ... F02K 9/24; F02K 9/72; F02K 9/346; F02K 9/38; G01N 3/10; G01N 2203/0044; G01N 2203/0212; G01N 2203/0274; G01N 2203/0676; G01N /; F05D 2220/80; F05D 2260/83
USPC .......................................................... 73/788
See application file for complete search history.

(56) References Cited

U.S. PATENT DOCUMENTS

| | | | | |
|---|---|---|---|---|
| 2,988,877 | A | * | 6/1961 | Shope ............... F02K 9/10 60/255 |
| 3,121,993 | A | | 2/1964 | Pennington |
| 3,533,485 | A | * | 10/1970 | Buffum, Jr. ......... F02K 9/96 73/599 |
| 3,583,162 | A | * | 6/1971 | Neely ............... F02K 9/343 60/255 |
| 3,662,592 | A | * | 5/1972 | Geisler ............ G01N 21/8803 73/104 |
| 3,937,070 | A | | 2/1976 | Briar |
| 4,664,234 | A | | 5/1987 | Wight |
| H682 | H | * | 10/1989 | Betts .......................... 73/86 |

(Continued)

FOREIGN PATENT DOCUMENTS

| | | |
|---|---|---|
| CN | 104820083 | 8/2016 |
| EP | 2581594 | 4/2013 |
| WO | 2017034773 | 3/2017 |

OTHER PUBLICATIONS

USPTO, Non-Final Office Action dated Apr. 7, 2021 in U.S. Appl. No. 16/386,099.

(Continued)

*Primary Examiner* — Octavia Hollington
(74) *Attorney, Agent, or Firm* — Snell & Wilmer L.L.P.

(57) ABSTRACT

A method for non-destructively determining a mechanical property of a solid rocket motor propellant grain may comprise applying, via a gas, a force to a surface of the solid rocket motor propellant grain, wherein a deformation is formed on the surface of the solid rocket motor propellant grain in response to the applying, and measuring a pressure of the gas. This process may be performed over time to determine a lifespan of the propellant grain.

17 Claims, 5 Drawing Sheets

(56) References Cited

U.S. PATENT DOCUMENTS

| | | | |
|---|---|---|---|
| 4,925,503 | A | 5/1990 | Canterberry et al. |
| 5,038,295 | A | 8/1991 | Husband et al. |
| 5,540,794 | A | 7/1996 | Willer et al. |
| 5,582,001 | A | 12/1996 | Bradford et al. |
| 6,966,264 | B2 * | 11/2005 | Solberg .................... F02K 9/38 102/381 |
| 7,077,011 | B2 * | 7/2006 | Johnson .................... F02K 9/34 73/760 |
| 7,652,488 | B1 | 1/2010 | Lopatin |
| 8,210,052 | B1 | 7/2012 | Biggs |
| 9,329,113 | B2 | 5/2016 | Neviere et al. |
| 2006/0032562 | A1 | 2/2006 | Wight et al. |
| 2008/0110274 | A1 | 5/2008 | Johnson et al. |
| 2013/0255223 | A1 | 10/2013 | Brady |
| 2016/0084059 | A1 * | 3/2016 | Moore ................. E21B 43/247 166/299 |

OTHER PUBLICATIONS

USPTO, Pre-Interview First Office Action dated Feb. 18, 2021 in U.S. Appl. No. 16/386,141.
USPTO, Restriction/Election Requirement dated Apr. 30, 2021 in U.S. Appl. No. 16/386,169.
USPTO, Notice of Allowance dated Jun. 10, 2021 in U.S. Appl. No. 16/386,141.
USPTO, Corrected Notice of Allowance dated Jun. 23, 2021 in U.S. Appl. No. 16/386,141.
European Patent Office, European Search Report dated Jun. 24, 2020 in Application No. 19213315.5.
European Patent Office, European Search Report dated Jul. 10, 2020 in Application No. 19214281.8.
European Patent Office, European Search Report dated Jul. 9, 2020 in Application No. 19213893.1.
Euorpean Patent Office, European Search Report dated Jul. 27, 2020 in Application No. 19216310.3.

* cited by examiner

IN-SITU SOLID ROCKET MOTOR PROPELLANT GRAIN AGING USING GAS

FIELD

The present disclosure relates generally to solid rocket motors, and more particularly, to systems and methods for assessing propellant grain lifespan.

BACKGROUND

Rocket propellant grains rely on a polymer binder for their structural integrity. Changes to structural integrity may be described by a change in mechanical properties that, in part, determines the propellant grain lifespan. While the chemical composition of a polymer type affects the way it ages, the changes in propellant grain mechanical properties due to polymer aging are a factor in determining propellant grain lifespan. One method of assessing the lifespan of a solid rocket motor is by destructively disassembling the solid rocket motor to measure mechanical properties of the propellant grain.

SUMMARY

A method for non-destructively determining a lifespan of a solid rocket motor propellant grain is disclosed, comprising applying a force to a surface of the solid rocket motor propellant grain via a gas, wherein a deformation is formed on the surface of the solid rocket motor propellant grain in response to the application of the force, and measuring a pressure of the gas.

In various embodiments, the propellant grain is a solid mass with an exposed inner surface area defining a perforation in the interior of the solid rocket motor propellant grain.

In various embodiments, the method further comprises determining the lifespan of the solid rocket motor propellant grain based upon the pressure of the gas.

In various embodiments, the method further comprises moving the gas into the perforation, wherein the force is applied to the surface in response to the gas being moved into the perforation of the solid rocket motor propellant grain.

In various embodiments, the gas is pressurized in response to moving a pre-determined number of moles of gas into the perforation, wherein the deformation is formed in response to the gas being pressurized.

In various embodiments, a pre-determined number of moles of the gas is moved into the perforation.

In various embodiments, the method further comprises calculating a value of a mechanical property of the solid rocket motor propellant grain based upon the deformation.

In various embodiments, the mechanical property comprises a bulk relaxation modulus (k) calculated using equation $$k = \frac{P}{\frac{\Delta V}{V_{initial}}},$$

where P is the measured pressure, $\Delta V$ is a change in volume of the perforation, and $V_{initial}$ is a volume of the perforation before it expands in response to the gas.

A method for non-destructively surveilling a mechanical property of a solid rocket motor propellant grain is disclosed, comprising applying a first force to a surface of the solid rocket motor propellant grain at a first time, wherein a first deformation is formed on the surface of the solid rocket motor propellant grain in response to the applying the first force, measuring a first value of a relaxation modulus of the solid rocket motor propellant grain based on the first deformation, applying a second force to the surface of the solid rocket motor propellant grain at a second time, wherein a second deformation is formed on the surface of the solid rocket motor propellant grain in response to the applying the second force, and measuring a second value of the relaxation modulus of the solid rocket motor propellant grain based on the second deformation, wherein at least one of the first force or the second force is applied to the surface by moving a gas into a perforation of the solid rocket motor propellant grain.

In various embodiments, the method further comprises comparing the first value with the second value.

In various embodiments, the method further comprises predicting a future value of the relaxation modulus based on a trend between the first value and the second value.

In various embodiments, the method further comprises determining a remaining lifespan of the solid rocket motor propellant grain based on a comparison between the future value and a pre-determined design threshold.

In various embodiments, the gas is pressurized in response to moving a pre-determined number of moles of gas into the perforation.

In various embodiments, at least one of the first deformation or the second deformation is formed in response to the gas being pressurized.

In various embodiments, the first value of the relaxation modulus is measured by measuring a pressure of the gas.

In various embodiments, the first value of the relaxation modulus is measured based upon an initial volume of the perforation and a second volume of the perforation.

In various embodiments, the first value of the relaxation modulus is calculated using an equation $P_2 V_{initial} = nRT$, where R is a universal gas constant of the gas, T is a temperature of the gas, n is a number of moles of the gas, $V_{initial}$ is an initial volume of the perforation, and $P_2$ is a measured pressure of the gas.

A solid rocket motor propellant grain arrangement is disclosed, comprising a case, a propellant grain disposed within the case, a perforation extending through the propellant grain, and a port in fluid communication with the perforation, wherein the perforation is configured to receive a gas via the port.

In various embodiments, the solid rocket motor propellant grain arrangement further comprises a conduit coupled to the port.

In various embodiments, the solid rocket motor propellant grain arrangement further comprises a pressure gauge in fluid communication with the perforation, via the port.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, and mechanical changes may be made without departing from the scope of the disclosure. Thus, the detailed description herein is presented for purposes of illustration only and not of limitation. For example, the steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected, or the like may include permanent, removable, temporary, partial, full, and/or any other possible attachment option. Additionally, any reference to without contact (or similar phrases) may also include reduced contact or minimal contact.

Figure 1:
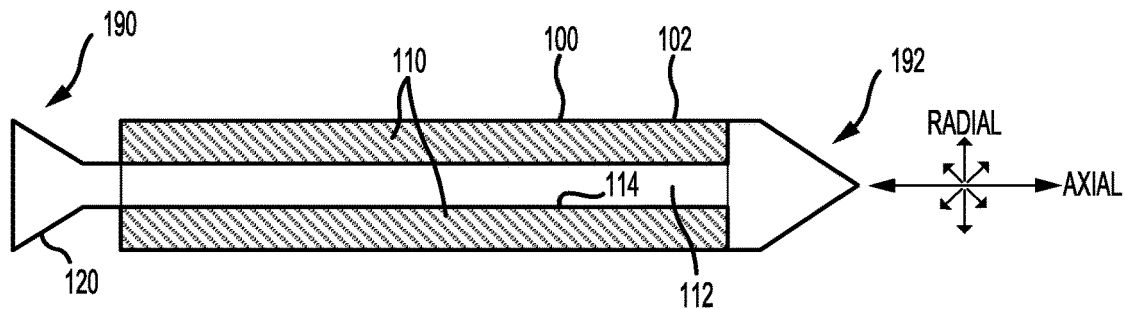
FIG. 1 illustrates a cross section view of a solid rocket motor comprising a propellant grain having a perforation, in accordance with various embodiments.

With reference to FIG. 1, a solid rocket motor 100 is illustrated, in accordance with various embodiments. Solid rocket motor 100 may comprise an aft end 190 and a forward end 192. Solid rocket motor 100 may comprise a casing 102 extending between aft end 190 and forward end 192. In various embodiments, casing 102 may comprise a cylindrical geometry. Solid rocket motor 100 may comprise a nozzle 120 disposed at aft end 190. Nozzle 120 may be coupled to casing 102. Solid rocket motor 100 may comprise a solid rocket motor propellant grain (propellant grain) 110 disposed within casing 102. In various embodiments, propellant grain 110 may be comprised of a solid fuel, such as a pure fuel, inert without an oxidizer. For example, propellant grain 110 may comprise a hydroxyl-terminated polybutadiene (HTPB), a polymethyl methacrylate (PMMA), or a polyethylene (PE), among others. In various embodiments, propellant grain 110 may be comprised of a composite propellant comprising both a fuel and an oxidizer mixed and immobilized within a cured polymer-based binder. For example, propellant grain 110 may comprise an ammonium nitrate-based composite propellant (ANCP) or ammonium perchlorate-based composite propellant (APCP). Propellant grain 110 may be a solid mass with an exposed inner surface area defining a perforation volume (also referred to herein as a perforation) in the interior of the solid rocket motor. In this regard, propellant grain 110 may comprise a perforation 112. Perforation 112 may be defined by a bore extending axially through propellant grain 110.

A mechanical property envelope may describe the minimum and maximum performance values necessary for a propellant grain to function as designed. The calculated mechanical property envelope is typically derived from a series of tests to determine propellant failure limits under various loading conditions. When a propellant sample mechanical property falls outside of the calculated envelope, the propellant grain service life is at an end.

The mechanical properties of the propellant comprising the grain can be measured both immediately after curing and after an accelerated aging period. Typically, the measurements are performed on propellant samples produced simultaneously with the production of propellant grains. Accelerated aging of the propellant samples is usually achieved through exposure to high temperatures for a duration of time designed to mimic the passage of time. The mechanical properties of the propellant grain contained within the rocket motor are typically assumed to be represented by the simultaneously produced propellant samples. The service life of the propellant grain is then assumed to be represented by the performance of the propellant samples subjected to accelerated aging, with a conservative reduction to compensate for potential variation between propellant sample and propellant grain.

To validate the typical assumption that the propellant grain within the rocket motor is accurately represented by the propellant samples, it may be desirable to calculate mechanical properties of a propellant grain to determine the health of the corresponding solid rocket motor. Typically, in order to determine the health of a plurality of solid rocket motors, a sacrificial solid rocket motor is disassembled using destructive means to gain access to the propellant of the sacrificial solid rocket motor in order to take proper measurements. The sacrificial solid rocket motor would typically be similar to the plurality of solid rocket motors (e.g., same type, age, storage conditions, etc.). Stated differently, a solid rocket motor is sacrificed in order to estimate the health of a plurality of similar solid rocket motors.

The present disclosure, as described herein, provides systems and methods for non-destructively surveilling solid rocket motor propellant grains for predicting the lifespan and the remaining lifespan of the solid rocket motor.

Figure 2:
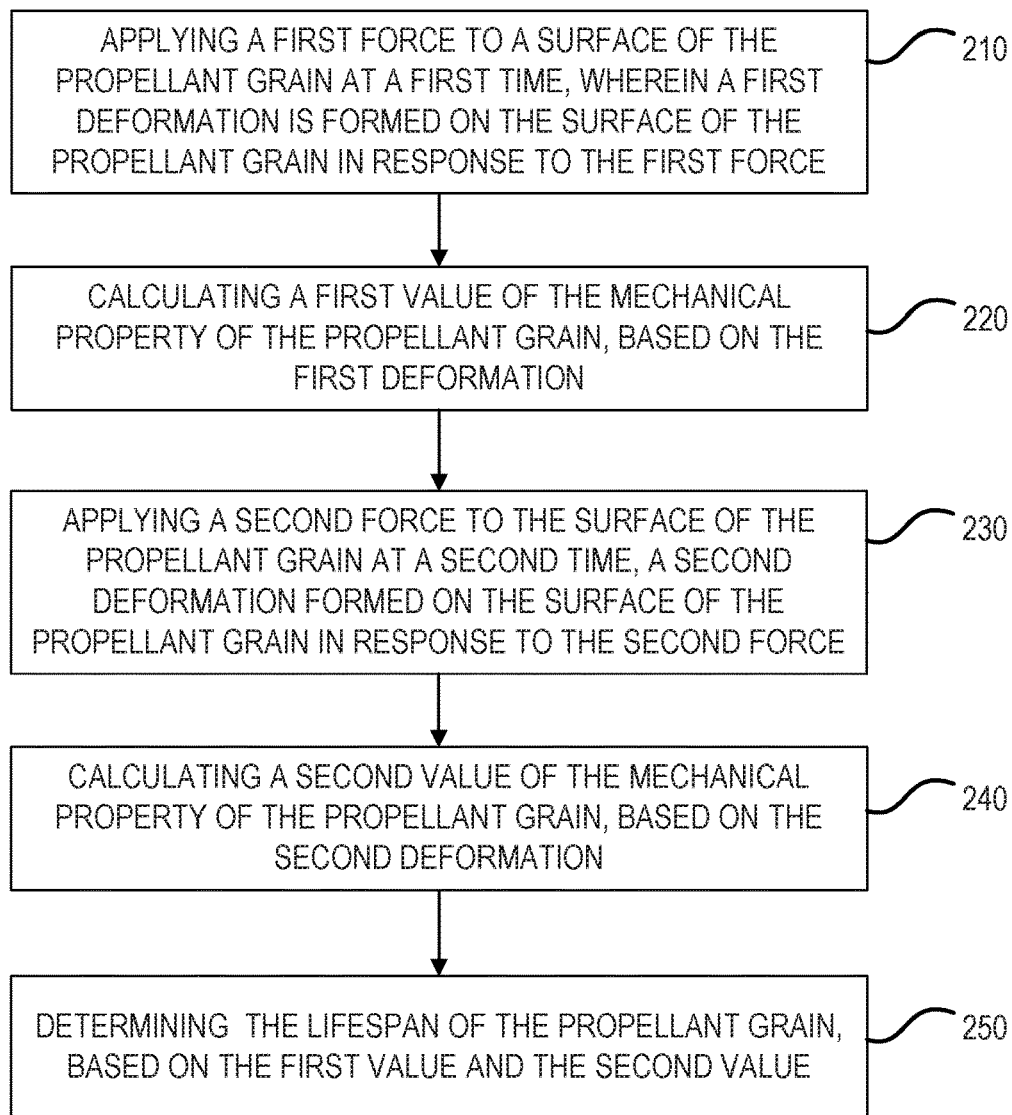
FIG. 2 illustrates a method for non-destructively surveilling a mechanical property of a solid rocket motor propellant grain, in accordance with various embodiments.

With reference to FIG. 2, a method 200 for non-destructively surveilling a mechanical property of a solid rocket motor propellant grain is illustrated, in accordance with various embodiments. Method 200 includes applying a first force to a surface of the propellant grain at a first time, wherein a first deformation is formed on the surface of the propellant grain in response to the first force (step 210). Method 200 includes calculating a first value of the mechanical property of the propellant grain, based on the first deformation (step 220). Method 200 includes applying a second force to the surface of the propellant grain at a second time, a second deformation formed on the surface of the propellant grain in response to the second force (step 230). Method 200 includes calculating a second value of the mechanical property of the propellant grain, based on the second deformation (step 240). Method 200 includes determining the remaining lifespan of the propellant grain, based on the first value and the second value (step 250) and through comparison of their values with the modeled performance minima and/or maxima.

With combined reference to FIG. 1 and FIG. 2, step 210 and step 230 may include applying a force to surface 114 of propellant grain 110. The force may be applied via a variety of devices and/or methods, as will be described with further detail herein. Surface 114 may be an inner surface of propellant grain 110. Surface 114 may be a radially displayed inner surface of propellant grain 110. Surface 114 may define perforation 112. Perforation 112 may comprise a bore formed through propellant grain 110. A deformation may be formed in propellant grain 110 in response to the force. For example, a deformation may be formed in surface 114 in response to the force. Step 220 and step 240 may include calculating a mechanical property of propellant grain 110, based upon the respective deformations. For example, a mechanical property that may be calculated is the bulk relaxation modulus (k) of propellant grain 110. As will be described with further detail herein, the amount of deformation of the propellant grain 110 in response to a given force, may indicate the magnitude of the bulk relaxation modulus (k) of propellant grain 110.

Figure 3A:
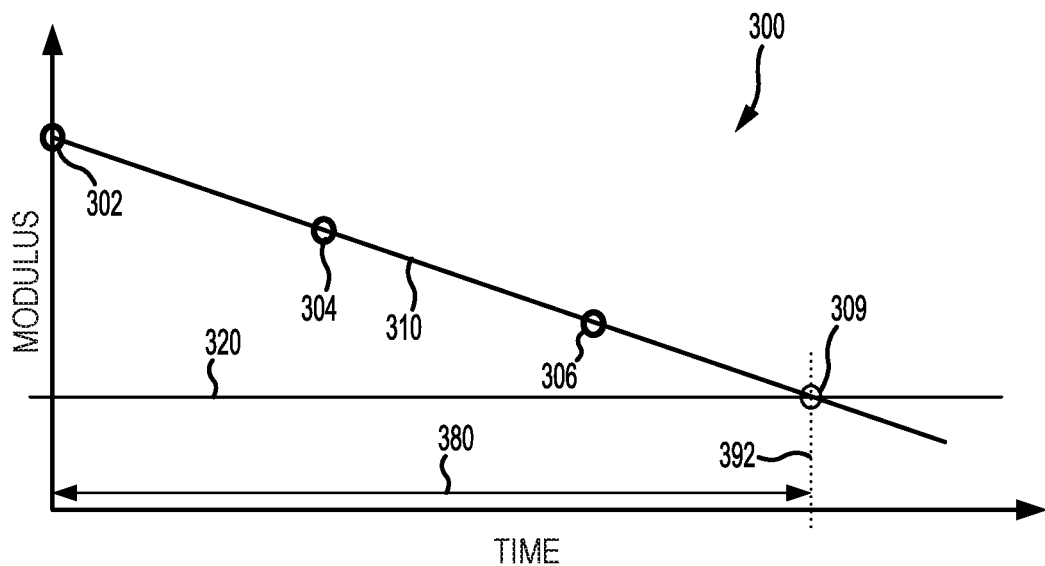
FIG. 3A and FIG. 3B illustrate plots of bulk relaxation modulus of a propellant grain versus time, in accordance with various embodiments.

In various embodiments, step 210 may occur at a first time and step 230 may occur at a second time. Similarly, step 220 may occur during the first time and step 240 may occur during the second time. For example, step 230 and step 240 may occur a year or more after step 210 and step 220. In this regard, the health of solid rocket motor 100 may be surveilled over a period of time. With additional reference to FIG. 3A, a plot 300 of various bulk relaxation modulus (k) values calculated over time is illustrated, in accordance with various embodiments. For example, first value 302 may be calculated at a first time, second value 304 may be calculated at a second time, and third value 306 may be calculated at a third time. A trend (also referred to herein as a curve) 310 may be determined based on first value 302, second value 304, and third value 306. For example, a curve of best fit (i.e., curve 310) may be determined using any suitable method including, but not limited to, interpolation, polynomial interpolation, smoothing, line fitting, curve fitting, extrapolation, analytic models, etc. Although illustrated as having three separate values, it is contemplated that curve 310 may be determined using two or more values. For example, using solely first value 302 and second value 304, or using more than three values.

Curve 310 may be used to determine a future value 309. For example, curve 310 may be compared with a pre-determined threshold value 320 of bulk relaxation modulus (k) and a time 392 at which curve 310 will intersect with pre-determined threshold value 320 may be used to define future value 309. In this regard, curve 310 may be extrapolated to estimate a time 392 at which the mechanical property (e.g., bulk relaxation modulus (k)) will reach the pre-determined threshold value 320. Value 320 can be determined by modeling and calculation, through measurement of propellant samples subjected to accelerated aging, or by destructive testing of a sacrificial solid rocket motor. In this regard, it may be determined that solid rocket motor 100 has a lifespan of duration 380. Duration 380 may be measured in units of time, such as years, months, or days, for example.

Figure 3B:
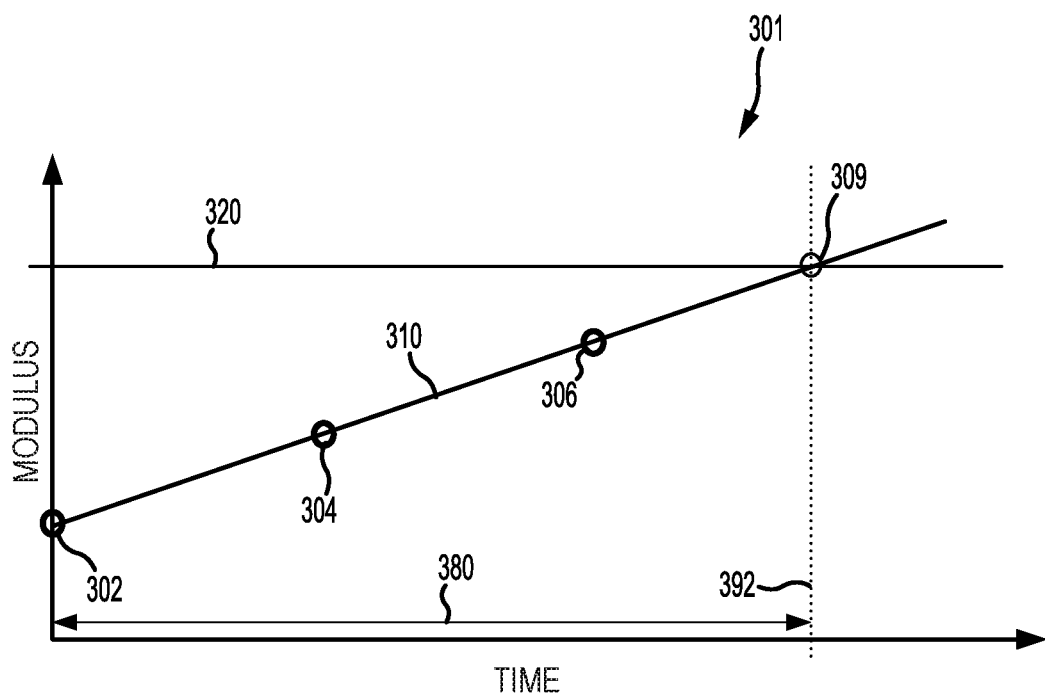

With reference to FIG. 3B, a plot 301 of various bulk relaxation modulus (k) values calculated over time is illustrated, in accordance with various embodiments. Plot 301 differs from plot 300 of FIG. 3A in that the propellant grain bulk relaxation modulus (k) of plot 301 increases over time. Thus, methods described herein may be suitable for propellant grains that have a bulk relaxation modulus (k) that increase or decrease over time. Stated differently, methods described herein may be suitable for propellant grains that soften or harden over time.

Figure 4:
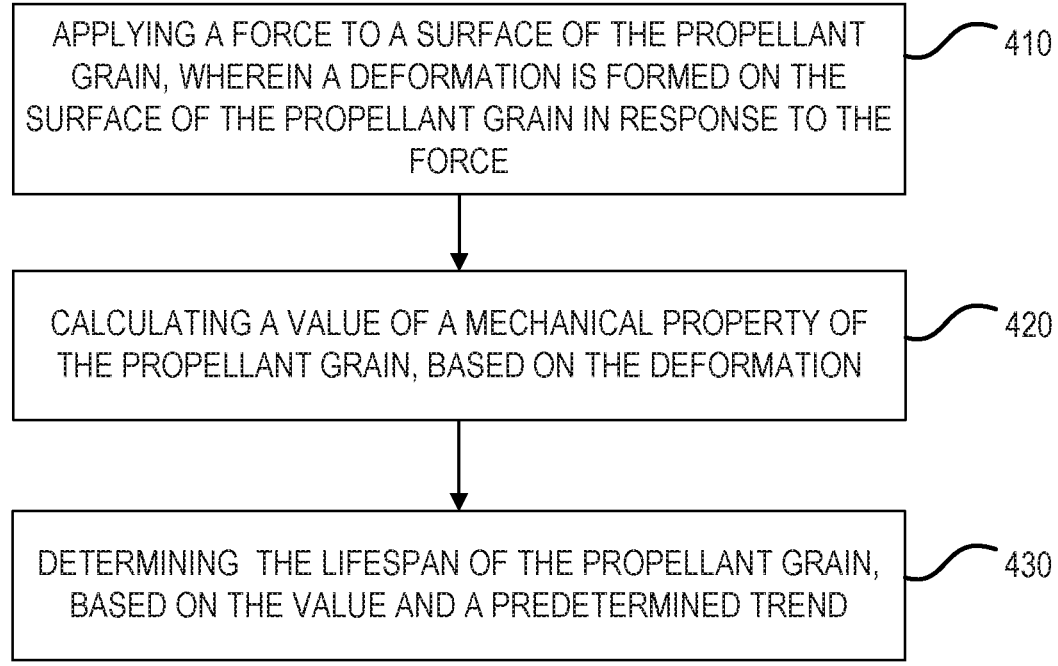
FIG. 4 illustrates a method for non-destructively surveilling a mechanical property of a solid rocket motor propellant grain, in accordance with various embodiments.

Having described a method for non-destructively surveilling a mechanical property of a solid rocket motor propellant grain using two measured values, it is contemplated herein that a method for non-destructively surveilling a mechanical property of a solid rocket motor propellant grain may be performed using only a single measured value. With reference to FIG. 4 a method 400 for non-destructively surveilling a mechanical property of a solid rocket motor propellant grain is illustrated, in accordance with various embodiments. Method 400 includes applying a force to a surface of the propellant grain, wherein a deformation is formed on the surface of the propellant grain in response to the force (step 410). Method 400 includes calculating a value of a mechanical property of the propellant grain, based on the deformation (step 420). Method 400 includes determining the remaining lifespan of the propellant grain, based on the calculated value and a predetermined trend (step 430).

Figure 5:
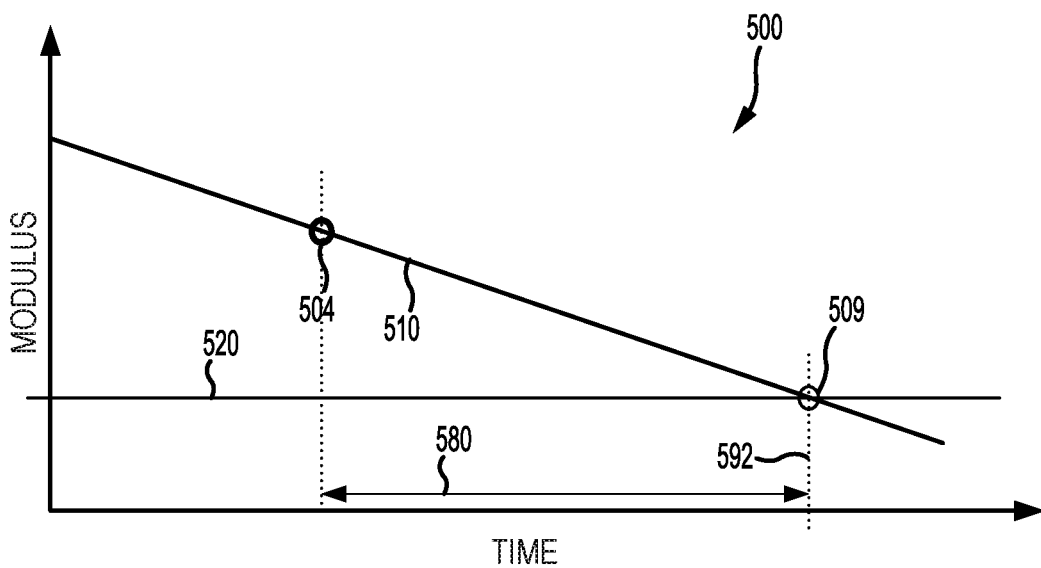
FIG. 5 illustrate plots of bulk relaxation modulus of a propellant grain versus time, in accordance with various embodiments.

With combined reference to FIG. 1 and FIG. 4, step 410 may include applying a force to surface 114 of propellant grain 110. Step 420 may include calculating a mechanical property of propellant grain 110, based upon the deformation. For example, a mechanical property that may be calculated is the bulk relaxation modulus (k) of propellant grain 110. Step 430 may include comparing the calculated bulk relaxation modulus (k) of propellant grain 110 with a predetermined trend which represents that of propellant grain 110, for example using a trend representing the performance (i.e., bulk relaxation modulus) of a propellant sample subjected to an accelerated aging process, or a trend calculated using a model produced by the structural analysis of the propellant grain. In various embodiments, the predetermined trend is determined by modeling and calculation, through measurement of propellant samples subjected to accelerated aging, and/or by destructive testing of a sacrificial solid rocket motor With additional reference to FIG. 5, a plot 500 of a calculated bulk relaxation modulus (k) value with respect to a predetermined trend is illustrated, in accordance with various embodiments. For example, value 504 may be calculated and compared with a predetermined trend (also referred to herein as a curve) 510 representing the change in bulk relaxation modulus of the propellant grain with respect to time. Curve 310 may be used to determine a future value 309. Curve 510 may be compared with a pre-determined threshold value 520 of bulk relaxation modulus (k) and a future time 592 at which curve 510 will intersect with pre-determined threshold value 520 may be used to define future value 509. In this regard, calculated value 504 may be superimposed with curve 510 to estimate a time 592 at which the mechanical property (e.g., bulk relaxation modulus (k)) will reach the pre-determined threshold value 520. Value 520 can be determined by modeling and calculation, through measurement of propellant samples subjected to accelerated aging, and/or by destructive testing of a sacrificial solid rocket motor. In this regard, it may be determined that solid rocket motor 100 has a remaining lifespan of duration 580. Duration 580 may be measured in units of time, such as years, months, or days, for example.

Figure 6:
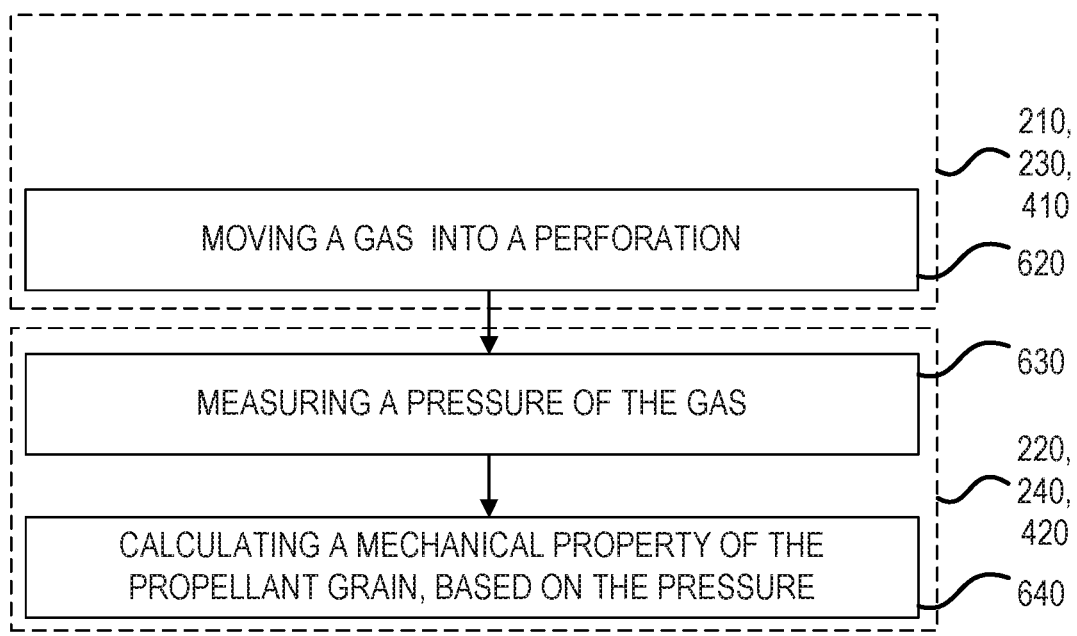
FIG. 6 illustrates sub-steps of the method of FIG. 2 and/or FIG. 4, including methods for applying a force (or pressure) to the propellant grain, as well as calculating the mechanical property, in accordance with various embodiments.
Figure 7A:
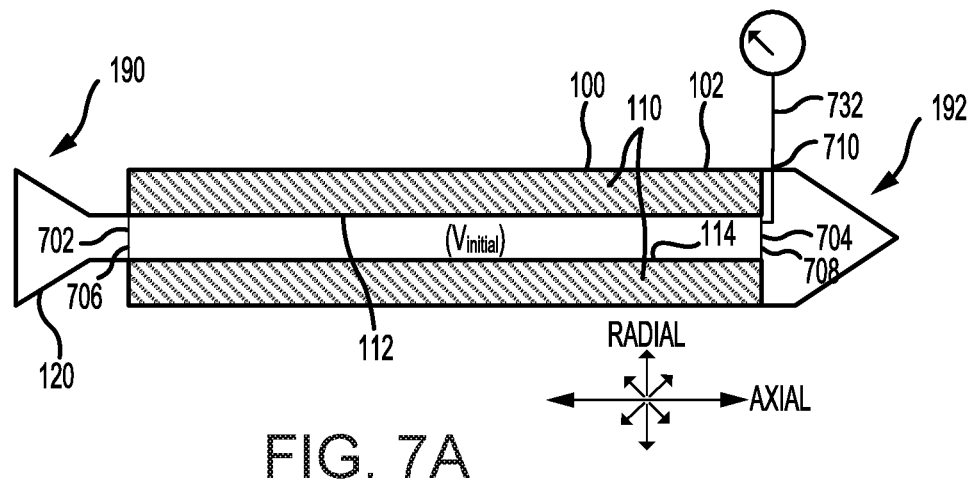
FIG. 7A illustrates a cross section view of the solid rocket motor of FIG. 1 with a port in fluid communication with the hermetically sealed perforation, in accordance with various embodiments.
Figure 7B:
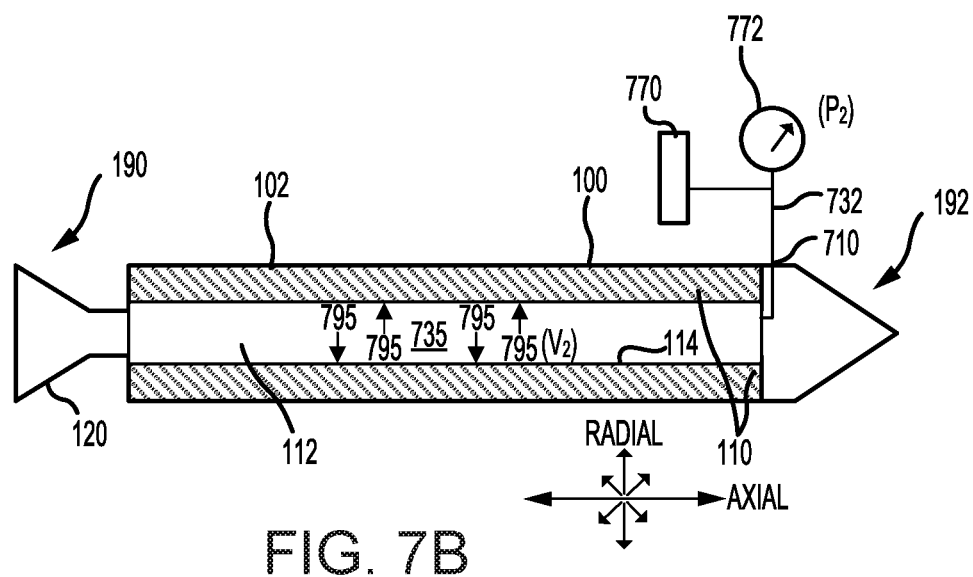
FIG. 7B illustrates a cross section view of the solid rocket motor of FIG. 7A with the perforation filled with a gas, the perforation having expanded in response to the pressurized gas, in accordance with various embodiments.

Having described methods for non-destructively surveilling a mechanical property of a solid rocket motor propellant grain for determining a lifespan of a solid rocket motor, FIG. 6 through FIG. 7B illustrate various methods for applying a force to the propellant grain, as well as calculating the mechanical property.

With reference to FIG. 6, step 210 and/or step 230 of method 200 of FIG. 2 and/or a step 410 of method 400 of FIG. 4 may include moving a gas into a perforation (sub-step 630). Step 220 and/or step 240 of method 200 of FIG. 2 and/or a step 420 of method 400 of FIG. 4 may include measuring a pressure of the gas (sub-step 630). Step 220 and/or step 240 of method 200 of FIG. 2 and/or a step 420 of method 400 of FIG. 4 may include calculating a mechanical property of the propellant grain, based on the pressure (sub-step 640).

With respect to FIG. 7A and FIG. 7B, elements with like element numbering, as depicted in FIG. 1, are intended to be the same and will not necessarily be repeated for the sake of clarity.

With reference to FIG. 7A, perforation 112 may be hermetically sealed at both axial ends thereof. In this regard, a first end 702 of perforation 112 may be sealed via a seal 706. Seal 706 may comprise any suitable hermetic seal, including rubber plugs, or glass-to-metal hermetic seals, among others. Seal 706 may be coupled to propellant grain 110 such that pressurized gas does not leak from perforation 112. Furthermore, second end 704 of perforation 112 may be hermetically sealed. The forward end wall 708 of casing 102 at second end 704 may hermetically seal perforation 112. In various embodiments, forward end wall 708 includes an ignitor for igniting propellant grain 110.

In various embodiments, solid rocket motor 100 includes a port 710 in fluid communication with perforation 112. With combined reference to FIG. 6A and FIG. 7A, sub-step 620 may include connecting a conduit 732, such as a hose for example, to port 710. Perforation 112 may comprise an initial volume ($V_{initial}$). With combined reference to FIG. 6A and FIG. 7B, sub-step 620 may include moving a gas 735 into perforation 112. Gas 735 may be any compressible gas including air, nitrogen, etc. A gas supply 770 may be connected to conduit 732 to supply the gas 735 to perforation 112. In various embodiments, gas supply 770 may comprise a gas cylinder. In various embodiments, sub-step 620 may include moving a pre-determined number of moles of gas 735 into perforation 112. Thus, gas 735 may be moved into perforation 112 in a controlled manner. Perforation 112 may expand in response to the gas 735 being moved into perforation 112. In this manner, all radial expansion of perforation 112 may correspond to deformation of propellant grain 110. For example, gas 735 may exert a force, depicted by arrows 795, on surface 114 which may cause surface 114 to expand. Force 795 may be exerted onto surface 114 of propellant grain 110 in response to gas 735 being moved into perforation 112. Thus, perforation 112 may comprise a volume ($V_2$) in response to being filled with gas 735. In this regard, a change in volume of perforation 112 may correspond to a volume of the deformation. The change in volume of perforation 112 may correspond to a mechanical property of propellant grain 110, such as the bulk relaxation modulus (k) of propellant grain 110 for example. Force 795 may be a relatively small force, causing a relatively small deformation, such that the deformation does not damage the performance of propellant grain 110.

Sub-step 630 may include measuring a pressure ($P_2$) of gas 735. A pressure gauge 772 may be used to measure pressure ($P_2$). In this regard, pressure gauge 772 may be in fluid communication with perforation 730. Pressure ($P_2$) may be the pressure of a pre-determined number of moles of gas 735 in perforation 730. The pressure ($P_2$) may vary in response to the bulk relaxation modulus (k) of propellant grain 110. For example, bulk relaxation modulus (k) may be defined per equation 1 below:

$$k = \frac{P}{\frac{\Delta V}{V_{initial}}}$$ EQ. 1 where k is the bulk relaxation modulus, P is the pressure applied by gas 735 to propellant grain 110, $\Delta V$ is the change in volume of perforation 730, and $V_{initial}$ is the initial volume of perforation 730 before expansion, such as is shown in FIG. 7A for example. In this regard, force 795 may be the product of pressure (P) and the area of the perforation 730 in contact with surface 114.

In this regard, $\Delta V$ may be defined by equation 2 below:

$$\Delta V = V_{initial} - V_2$$ EQ. 2 where $V_2$ is the volume of perforation 730 after being filled with the pre-determined number of moles of gas 735.

In various embodiments, the initial volume ($V_{initial}$) is a known value. In various embodiments, the initial volume ($V_{initial}$) is calculated by moving a known number of moles of gas (n), at a known temperature (T) into perforation 730 at a low, measured pressure ($P_{meas}$) (i.e., low enough such that the volume of perforation 730 does not increase in response to the low pressure), and calculating V using equation 3 below.

Using the known initial volume, the expected pressure ($P_{calc}$) of gas 735 can be determined using equation 3:

$$P_{calc}V = nRT$$ EQ. 3 where R is the universal gas constant of gas 735, T is the temperature of gas 735, n is the number of moles of gas 735, and V is the initial volume ($V_{initial}$) of perforation 112. The expected pressure ($P_{calc}$) is then compared with the measured pressure ($P_2$) and the difference in pressures (i.e., $P_{calc} - P_2$) is noted. The difference from ideality is due to the compression of the propellant grain 110 under pressure of gas 735. Stated differently, the calculated pressure ($P_{calc}$) and the measured pressure ($P_2$) may be slightly different for controlled additions of gas (varying n) in response to the propellant grain being compressed which in turn will create a slightly larger volume (and reduced pressure) for the gas 735 to occupy. The difference between calculated pressure ($P_{calc}$) and the measured pressure ($P_2$) may be used to determine the remaining lifespan of propellant grain 110. In this regard, the Y-axis of FIG. 3A, FIG. 3B, and FIG. 5 may be "pressure ($P_2$)" instead of "modulus" or pressure difference ($P_{calc} - P_2$) instead of "modulus." However, it is understood herein that, in various embodiments, the pressure ($P_2$) corresponds to the modulus of propellant grain 110. In this regard, the modulus of propellant grain 110 may be calculated based upon the measured pressure ($P_2$).

In various embodiments, the ambient temperature and atmospheric pressure is known so that any change in temperature or atmospheric pressure between calculation may be taken into account.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for non-destructively determining a lifespan of a solid rocket motor propellant grain, wherein the solid rocket motor propellant grain is a solid mass with an exposed inner surface defining a perforation in the interior of the solid rocket motor propellant grain, the method comprising:

applying a force to the inner surface of the solid rocket motor propellant grain via a gas, wherein a deformation is formed on the inner surface of the solid rocket motor propellant grain in response to the application of the force;

measuring a pressure of the gas;

calculating a value of a mechanical property of the solid rocket motor propellant grain based upon a change in volume of the perforation and the pressure of the gas; and determining the lifespan of the solid rocket motor propellant grain based upon the value of the mechanical property.

2. The method of claim 1, further comprising:

moving the gas into the perforation, wherein the force is applied to the inner surface in response to the gas being moved into the perforation of the solid rocket motor propellant grain.

3. The method of claim 2, wherein the gas is pressurized in response to moving a pre-determined number of moles of gas into the perforation, wherein the deformation is formed in response to the gas being pressurized.

4. The method of claim 3, wherein a pre-determined number of moles of the gas is moved into the perforation.

5. The method of claim 1, wherein the mechanical property comprises a bulk relaxation modulus (k) calculated using equation $$k = \frac{P}{\frac{\Delta V}{V_{initial}}},$$

where P is the measured pressure, $\Delta V$ is the change in volume of the perforation, and $V_{intitial}$ is a volume of the perforation before it expands in response to the gas.

6. A method for non-destructively surveilling a mechanical property of a solid rocket motor propellant grain, comprising:

applying a first force to a surface of the solid rocket motor propellant grain at a first time, wherein a first deformation is formed on the surface of the solid rocket motor propellant grain in response to the applying the first force;

measuring a first value of a relaxation modulus of the solid rocket motor propellant grain based on the first deformation;

applying a second force to the surface of the solid rocket motor propellant grain at a second time, wherein a second deformation is formed on the surface of the solid rocket motor propellant grain in response to the applying the second force; and measuring a second value of the relaxation modulus of the solid rocket motor propellant grain based on the second deformation, wherein at least one of the first force or the second force is applied to the surface by moving a gas into a perforation of the solid rocket motor propellant grain.

7. The method of claim 6, further comprising comparing the first value with the second value.

8. The method of claim 7, further comprising predicting a future value of the relaxation modulus based on a trend between the first value and the second value.

9. The method of claim 8, further comprising determining a remaining lifespan of the solid rocket motor propellant grain based on a comparison between the future value and a pre-determined design threshold.

10. The method of claim 6, wherein the gas is pressurized in response to moving a pre-determined number of moles of gas into the perforation.

11. The method of claim 10, wherein at least one of the first deformation or the second deformation is formed in response to the gas being pressurized.

12. The method of claim 11, wherein the first value of the relaxation modulus is measured by measuring a pressure of the gas.

13. The method of claim 12, wherein the first value of the relaxation modulus is measured based upon an initial volume of the perforation and a second volume of the perforation.

14. The method of claim 11, wherein the first value of the relaxation modulus is calculated using an equation $P_2 V_{initial} = nRT$, where R is a universal gas constant of the gas, T is a temperature of the gas, n is a number of moles of the gas, $V_{initial}$ is an initial volume of the perforation, and $P_2$ is a measured pressure of the gas.

15. A solid rocket motor propellant grain arrangement, comprising:
- a case;
- a propellant grain disposed within the case;
- a perforation extending through the propellant grain, wherein the perforation is hermetically sealed at each of its axial ends; and
- a port in fluid communication with the perforation, wherein the perforation is configured to receive a gas via the port while the perforation remains hermetically sealed so as to expand the perforation.

16. The solid rocket motor propellant grain arrangement of claim 15, further comprising a conduit coupled to the port.

17. The solid rocket motor propellant grain arrangement of claim 16, further comprising a pressure gauge in fluid communication with the perforation, via the port.

* * * * *